United States Patent [19]

Alagy et al.

[11] Patent Number: 5,235,117
[45] Date of Patent: Aug. 10, 1993

[54] PROCESS FOR THE PREPARATION OF BORIC OXIDE BY HYDROLYSIS OF METHYL BORATE AND ITS USE IN THE OXIDATION OF ALCOHOL-SATURATED HYDROCARBONS

[75] Inventors: Jacques Alagy; Christian Busson, both of Charbonnieres; Lionel Asselineau, Paris, all of France

[73] Assignee: Institut Francais du Petrole, Rueil Malmaison, France

[21] Appl. No.: 765,276

[22] Filed: Sep. 25, 1991

[30] Foreign Application Priority Data

Sep. 25, 1990 [FR] France ................... 90 11910
Oct. 8, 1990 [FR] France ................... 90 12473

[51] Int. Cl.$^5$ .................. B01D 3/34; C07C 35/08
[52] U.S. Cl. ..................... 568/837; 203/51; 203/70; 423/278; 568/821; 568/912
[58] Field of Search ............ 423/278; 568/887, 910.5, 568/912, 837, 821; 203/51, 52, 70

[56] References Cited

U.S. PATENT DOCUMENTS

| | | | |
|---|---|---|---|
| 2,642,453 | 6/1953 | Lippincott | 203/52 |
| 2,833,623 | 5/1958 | May et al. | 568/887 |
| 2,880,144 | 3/1959 | Bush | 203/70 |
| 3,086,039 | 4/1963 | Carter | 203/70 |
| 3,243,449 | 3/1966 | Winnick | 568/912 |
| 3,516,788 | 6/1970 | Fusby | 423/278 |
| 3,665,028 | 5/1972 | Russell | 568/912 |
| 3,796,761 | 3/1974 | Marcell et al. | 568/837 |
| 4,058,565 | 11/1977 | Thiel et al. | 568/837 |
| 4,908,196 | 3/1990 | Vasconi et al. | 423/278 |

OTHER PUBLICATIONS

R. F. Nickerson, "Heat of Complexing of Boric Acid from Hydrolysis of Methyl Borate", J. Inorg. Nucl. Chem., 1971, vol. 33, pp. 1665–1671.

Primary Examiner—Wayne Langel
Attorney, Agent, or Firm—Millen, White, Zelano & Branigan

[57] ABSTRACT

For preparing at least one boric oxide in an anhydrous or hydrated form and of general formula $B_2O_3, xH_2O$, in which x is a number from 0 to 3, a methyl borate hydrolyzate comprising boric oxide and methanol is introduced into a distillation column is introduced the product from, at least one compound (preferably a hydrocarbon such as, e.g., 2,3-dimethyl butane or 2-methyl pentane) forming a heteroazeotrope with methanol, said heteroazaeotrope having a boiling point below that of the azeotrope formed by methyl borate with methanol and at least one compound having a boiling point higher than that of methyl borate, said compound not forming an azeotrope with a boiling point below that of said heteroazeotrope and then at the head of the column said heteroazeotrope is recovered and at the bottom of the column a suspension containing at least one boric oxide.

A description is also given of a process for the oxidation of at least one saturated hydrocarbon into a product incorporating the corresponding alcohol wherein oxidation is carried out with oxygen in the presence of a boric oxide with. The oxidation product is hydrolyzed into orthoboric acid and alcohol, which is recovered by separation from the organic phase. The aqueous phase containing the boric acid is fed into a methyl borate formation zone and the methyl borate is recovered in the form of its azeotrope with methanol. The recovery of the boric oxide from said azeotrope is performed in accordance with the aforementioned process, the recovered boric oxide being recycled to the oxidation stage.

23 Claims, 1 Drawing Sheet

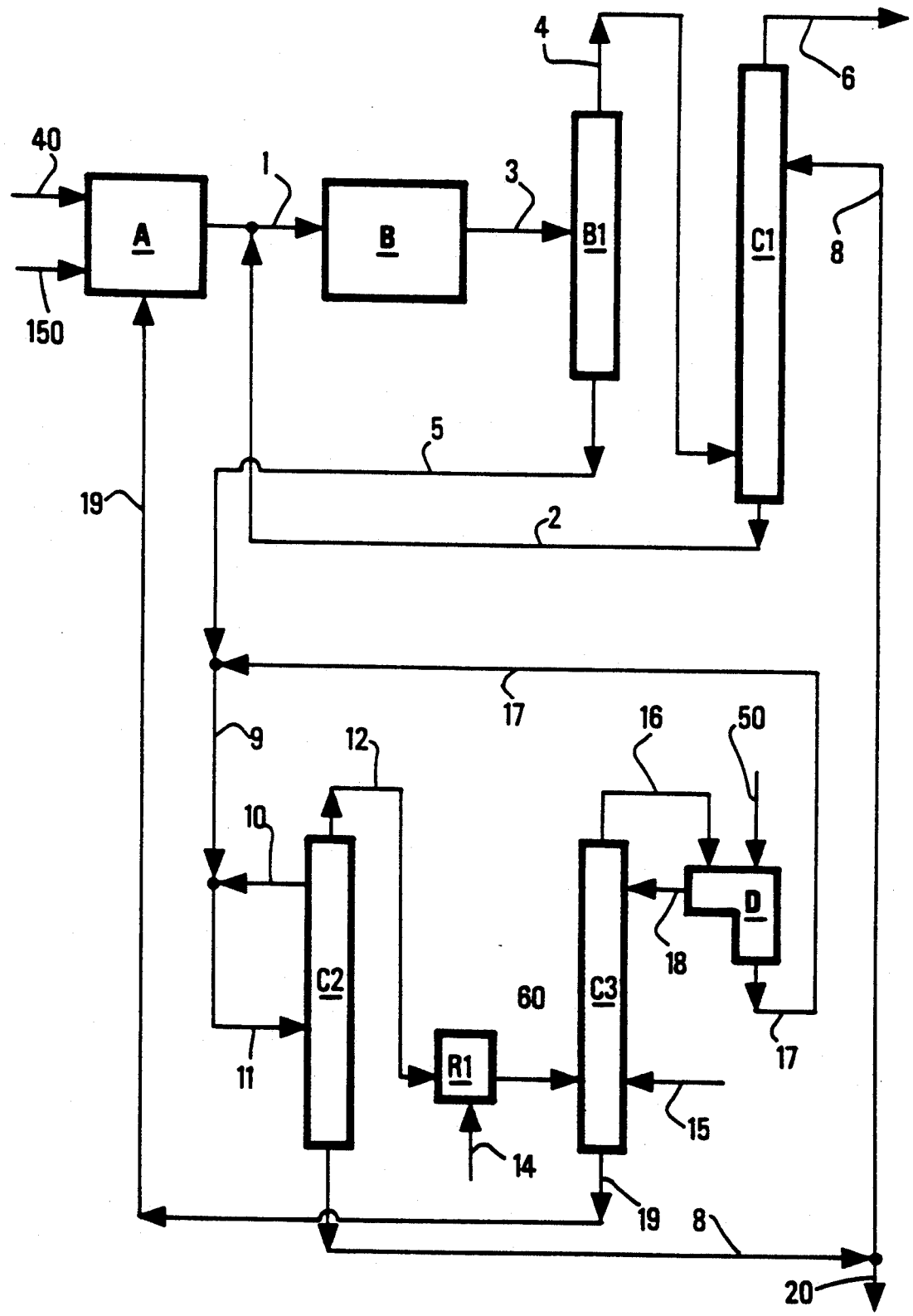

PROCESS FOR THE PREPARATION OF BORIC OXIDE BY HYDROLYSIS OF METHYL BORATE AND ITS USE IN THE OXIDATION OF ALCOHOL-SATURATED HYDROCARBONS

BACKGROUND OF THE INVENTION

This invention relates to a process for the preparation of boric oxide in anhydrous or hydrated form from methyl borate or a mixture of methyl borate and a third substance, e.g. a solvent of methyl borate such as in particular methanol.

The invention also relates to a process for the oxidation of saturated hydrocarbons with a product incorporating the alcohols corresponding to these hydrocarbons and more particularly a process for the oxidation of at least one saturated hydrocarbon selected from the group consisting of cyclohexane and cyclic and acyclic saturated hydrocarbons having 7 to 20 carbon atoms in their molecule, said oxidation being performed with the aid of a gas containing molecular oxygen in the presence of at least one boron compound forming esters with the alcohol formed during oxidation and said process incorporating a recovery of the boron compounds from the boric esters obtained and a reuse of these compounds in the oxidation stage.

The boron compounds of general formula (I) $B_2O_3$, $xH_2O$, in which x represents a number from 0 to 3 are compound described in the prior art and which are in particular used as a coreagent for the oxidation of saturated hydrocarbons with alcohols and ketones. In these oxidation reactions, the boron-based coreagent most frequently used comprises a majority of boron compound of general formula (I) in which x is equal to 1 and normally known as metaboric acid. This coreagent, which is generally insoluble in the reaction medium is preferably in an extremely divided form, so as to have a maximum chemical activity and the level of organic impurities present is preferably as low as possible, because they are prejudicial to the oxidation and often lead to a significant fouling of the reactors.

The hydrolysis of methyl borate in the presence or absence of methanol is a known process and is in particular described by R. F. NICKERSON in J. Inorg. Nucl. Chem., 1971, vol. 33, pp 1165-1671. This hydrolysis reaction is a balanced complex reaction more particularly supplying a mixture able to contain the various compounds of formula (I). According to NICKERSON, it not possible to displace the hydrolysis equilibrium by recovery of the compound or compounds formed as a result of a very significant boron loss during evaporation. Moreover, the displacement of the equilibrium by a mere distillation of the methanol formed during the hydrolysis reaction is not possible due to the minimum boiling point azeotrope which this compound forms with methyl borate.

SUMMARY OF THE INVENTION

The process for the preparation of at least one boric oxide in anhydrous or hydrated form of general formula (I) according to the present invention, makes it possible to obtain with a very good conversion normally higher than 95 molar % and most frequently approximately 100%, a very highly divided and relatively pure product. When the product formed by hydrolysis of methyl borate of formula $B(OCH_3)_3$ has to be used as an oxidation coreagent, it is normally preferable to choose the operating conditions and in particular the water quantity used relative to the methyl borate quantity used, in such a way that it contains less than 70% and preferably less than 50% and most frequently less than 30% by weight orthoboric acid of formula $H_3BO_3(B_2O_3, 3H_2O)$.

The sole FIGURE of the Drawing represents a flow scheme for carrying out the process according to the invention.

More specifically, the present invention relates to a process for the preparation of at least one boric oxide in anhydrous or hydrated form and of general formula $B_2O_3$, $xH_2O$, in which x is a number from 0 to 3, by methyl borate hydrolysis, in which into a hydrolysis zone are introduced methyl borate and water in a molar ratio of at least 1.3 mole of water, preferably at least 1.5 mole of water, per mole of methyl borate and then into a distillation column is introduced the product from the hydrolysis zone, incorporating said boric oxide and methanol (formed by hydrolysis of methyl borate) and at least one compound forming a heteroazeotrope with the methanol, said heteroazeotrope having a boiling point below that of the methyl borate-methanol azeotrope, characterized in that:

into said column is also introduced at least one compound having a boiling point above that of methyl borate, said compound not forming an azeotrope with a boiling point below that of said heteroazeotrope, at the head of the column the heteroazeotrope is recovered and is fed into a decanter in which separation takes place of the methanol from the compound forming the said heteroazeotrope and said compound is recycled in the distillation column as a charge for the latter and reflux and at the bottom of the column is recovered a mixture of at least one boric oxide in anhydrous or hydrated form and the compound having a boiling point higher than that of methyl borate.

The hydrolysis reaction in particular makes it possible to obtain oxides of general formula (I), in which x is equal to 0, 1 or 3 and often respectively known as boric anhydride ($B_2O_3$), metaboric acid ($HBO_2$ or $B_2O_3$, $H_2O$) and orthoboric acid ($H_3BO_3$ or $B_2O_3$, $3H_2O$). One of the main factors making it possible to orient this hydrolysis reaction towards a preferred formation of one of these oxides is the quantity of water used compared with the methyl borate quantity. Thus, when it is wished to obtain a hydrolysis product mainly containing metaboric acid, it is desirable to used a water quantity close to 2 moles of water per mole of methyl borate, e.g. approximately 1.8 to approximately 2.2 moles of water per mole of methyl borate. In the case where it is wished to obtain a product containing a majority of boric anhydride, it is desirable for the water quantity to be close to the theoretical quantity of 1.5 mole of water per mole of methyl borate necessary for the formation of said product. In the same way, if the water quantity is close to or greater than the theoretical water quantity of 3 moles of water per mole of methyl borate necessary for the formation of orthoboric acid, the hydrolyis product will contain said acid in majority form.

During the methyl borate hydrolysis reaction, it is most frequent to use a water quantity such that the water/methyl borate molar ratio is approximately 1.5:1 to approximately 2.5:1 and preferably approximately 1.8:1 to approximately 2.2:1.

Among the compounds forming with methanol a heteroazeotrope having a boiling point below the boiling point of the methanol-methyl borate azeotrope and whereof a non-exhaustive list is provided in the book Azeotropic Data, Advances in Chemistry Series 6, American Chemical Society, Washington USA, preference is given to the choice of those forming a heteroazeotrope containing at least 10% by weight methanol in the heteroazeotrope. Among the compounds forming with methanol a heteroazeotrope having a boiling point below the boiling point of the methanol-methyl borate azeotrope, it is also preferable to choose those whose heteroazeotrope has a boiling point at least 2° C. below the boiling point of the methanol-methyl borate azeotrope.

Usually the compounds forming said heteroazeotrope are chosen from among the hydrocarbons and preferably those having 4 to 6 carbon atoms in their molecule and no 6-member cycle. As a non-limitative example of such hydrocarbons, reference can be made to 2-methyl pentane and 2,3-dimethyl butane.

The quantity of compounds used in the present invention for forming the heteroazeotrope with the methanol is normally at least equal to the theoretical quantity necessary for azeotropically removing all the methanol present in the column, as well as that forming during hydrolysis. The quantity of said compound will usually exceed this theoretical quantity and will e.g. be approximately 1.1 time to approximately twice the theoretical quantity. If necessary, in the process in continuous manner, the quantity of said compound will be kept substantially constant by supplying continuously or in bursts a given quantity of said compound.

In an advantageous embodiment of the invention, the decanter will be supplied continuously or in bursts with a small proportion of water which will permit an easier separation of the layers. The water quantity used is normally approximately 0.5 to approximately 10% by weight, preferably approximately 1 to approximately 5% by weight and most frequently approximately 2 to approximately 4% by weight, based on the methanol weight.

The oxide or oxides forming during the hydrolysis are products obtained at the bottom of the column in the form of an extremely divided solid, conventionally in the form of a sol, suspended in the compound with the boiling point higher than that of the methyl borate introduced into said column. When hydrolysis is performed continuously, said compound is introduced continuously or in bursts, usually in a quantity equivalent to that which is drawn off for recovering the oxide or oxides formed. It is conventional practise to operate so as to obtain a suspension containing 1 to 50 and preferably 5 to 30 and most frequently 10 to 20% by weight solid, based on the total weight of the suspension. This compound is normally introduced into the column in the vicinity of its bottom and preferably into the reboiler.

The compound with the boiling point higher than that of methyl borate used is preferably a compound with a boiling point higher by at least 2° C. and most frequently at least 10° C. than that of methyl borate. This compound is most frequently chosen from among the hydrocarbons and preferably from within the group formed by cyclohexane and saturated hydrocarbons having 7 to 20 carbons atoms in their molecule.

The starting product used for the preparation of at least one boron oxide in the present invention is conventionally selected from the group consisting of methyl borate, the methyl borate-methanol azeotrope and a mixture of methanol-methyl borate containing more than 1 mole of methanol per mole of methyl borate. This starting product can be that resulting from the reaction of the orthoboric acid of formula $H_3BO_3$ with a methanol excess, based on the theoretical quantity necessary for the formation of the methyl borate and optionally in the presence of water. Use is normally made of at least 4 moles of methanol per mole of orthoboric acid. The methanol:orthoboric acid molar ratio if e.g.,, 4:1 to 20:1, preferably 5:1 to 10:1 and usually use is made of a methanol quantity such that said ratio is approximately 6:1. The use of a methanol excess like that defined hereinbefore makes it possible to obtain the methyl borate-methanol azeotrope which is recovered at the head of a distillation column. This methyl borate-methanol azeotrope contains 76.5% by weight methyl borate (i.e. one mole of methyl borate per mole of methanol). The methyl borate used could contain unconverted orthoboric acid without any major disadvantage for the satisfactory operation of the process, because this compound will then be recovered at the bottom of the column, usually in the reboiler with the oxide or oxides formed during hydrolysis. By operating with a methanol excess, e.g. in an adiabatic-type reactive column, at a temperature of approximately 70° C., the orthoboric acid conversion exceeds 99% and usually exceeds 99.5%. Thus, the unconverted orthoboric acid quantity which can be recovered at the bottom of the column is very small.

Preparation of methyl borate is widely described in the prior art and in particular in the following patents: U.S. Pat. No. 2,217,354, U.S. Pat. No. 2,808,424, U.S. Pat. No. 2,813,115 and U.S. Pat. No. 2,947,776.

The hydrolysis zone of the methyl borate can be a conventional reactor, which is preferably perfectly stirred, in which the methyl borate hydrolysis at least partly takes place, e.g. up to an equilibrium corresponding to the various conditions used, such as e.g. the water quantity introduced compared with the boric acid quantity and the temperature. Hydrolysis can also at least partly take place in the distillation column feedline, or in the lower part of the distillation column, e.g. in the reboiler, and said line or said column portion forms the said hydrolysis zone and then serves as a hydrolysis reactor.

When it is not wished to form a majority of orthoboric acid, it is desirable to choose operating conditions which make it possible to avoid local high water concentrations, which may lead to the preferred formation thereof and/or to work at a relatively high temperature, e.g. at least 120° C. at which said orthoboric acid dehydrates into metaboric acid. The hydrolysis is usually performed under conventional conditions, normally at a pressure between atmospheric pressure and approximately 20 megapascals (MPa) and most often at approximately 1.05 to approximately 10 MPa and preferably approximately 2 to approximately 4 MPa. The temperature at which the hydrolysis is performed is normally between ambient temperature (e.g. approximately 18° C.) and approximately 200° C. and preferably, particularly in the case where it is not wished to form a majority of orthoboric acid, approximately 100 to approximately 180° C. and most frequently approximately 120 to approximately 140° C. In all these cases, the hydrolysis continues within the distillation column by displacement of the equilibrium as a result of the removal of the methanol and the molar conversion of methyl borate usually exceeds 95%.

The distillation column is used in the present invention is a conventional column normally having approximately 20 to approximately 100 theoretical plates, most frequently approximately 30 to approximately 70 theoretical plates and preferably approximately 40 to approximately 60 theoretical plates. This column and in particular the lining of the stripping zone, when the latter is provided with the same, is chosen in such a way as to be able to operate, at least in the stripping zone, in the presence of a solid. The column charging zone is not very critical. It is possible to introduce the charge, which generally comprises methyl borate and/or methyl borate-methanol azeotrope and water, or which comprises the product from the hydrolysis reactor, at the bottom of the column or in the reboiler or in an intermediate zone of the column. The charge will preferably be introduced above the first theoretical plate and generally above a zone constituting a stripping zone for said column, said stripping zone normally having 1 to 10 and most frequently 2 to 5 theoretical plates. Above this stripping zone, the column incorporates an enrichment zone normally having 20 to 60 and usually 30 to 50 theoretical plates. The compound having the boiling point higher than that of methyl borate is normally introduced at the bottom of the column and e.g. at the level of or in the immediate vicinity of the reboiler. The compound forming the heteroazeotrope with the methanol is normally introduced in the vicinity of the top of the column or into the decanter, in which said compound is separated from methanol. When it is necessary to add a certain quantity of this compound during the operation of the unit, it is then preferable to introduce it into the decanter.

The distillation conditions are conventional conditions, which can easily be determined by the Expert as a function of the various compounds present in the column. Thus, it is possible to distil under a pressure below atmospheric pressure, at atmospheric pressure or under a pressure higher than atmospheric pressure. The reflux level is conventionally approximately 0.5 to approximately 5. The temperature in the reboiler is dependent on the compound having a boiling point higher than that of the methyl borate used in the process. Under the in particular pressure conditions chosen for the distillation, said temperature at the reboiler is normally at the most equal to the boiling point of said compound and exceeds the boiling point of the methyl borate. Preferably, said temperature exceeds by at least 10° C. the boiling point of methyl borate.

The example is illustrative and in no way limitative.

EXAMPLE 1

Into a perfectly stirred reactor heated to 125° C. and operating under an absolute pressure of 2 MPa, are continuously injected 135.8 kg/h (kilograms per hour) of a mixture of methyl borate and methanol containing 76.43% by weight of methyl borate (equimolar mixture) and 36 kg/h of water. The residence time of the mixture in the reactor is fixed at 10 minutes. The reactor effluent is continuously introduced into a distillation column operating under atmospheric pressure. This column has 43 theoretical plates and the effluent is introduced at ¼ of the total height of the column as from its base. At the bottom of the column are also continuously introduced 248.2 kg/h of cyclohexane. The compound used for forming a heteroazeotrope with a boiling point below that of the methyl borate-methanol azeotrope is 2,3-dimethyl butane, which is introduced into the column on starting up the operations. This compound forms with methanol a heteroazeotrope having 20% by weight methanol and whose boiling point is 45° C. In the condenser of the product recovered at the head of the column is introduced in a continuous manner 3.8 kg/h of water. The condensed product is fed into a decanter, in which recovery takes place of a heavy phase containing the water introduced into the condenser and virtually all the methanol produced (resulting from the hydrolysis of the methyl borate) and/or introduced into the column at the same time as the hydrolysis effluent. The heavy phase quantity recovered in the decanter is 131.8 kg/h. The light phase is 2,3-dimethyl butane containing traces of methanol and is supplied as reflux to the head of the column. The reflux level is maintained constant throughout the operation and is equal to 1. At the bottom of the column and at a temperature of 81° C. are drawn off 292 kg/h of a suspension in cyclohexane and containing 15% by weight of a very finely divided solid, which is essentially pure metaboric acid.

Another object of the invention is a process for the oxidation of hydrocarbons into the corresponding alcohols in the presence of boric oxide, during which the boric oxide is converted into boric acid and then methyl borate from which the boric oxide is regenerated by using the aforementioned process.

The production of alcohols by the oxidation of hydrocarbons by a gas containing molecular oxygen is, for a number or years now, performed in the presence of a boron compound forming esters with the alcohol, so as to increase the alcohol selectivity by limiting the subsequent oxidation of the alcohol formed, e.g. to the ketonic compound. These processes require the hydrolysis of the boric esters formed, so as to recover the sought alcohol and, for economic reasons and for avoiding pollution problems, the recovery and recycling of the orthoboric acid, formed during hydrolysis, to the oxidation stage.

Numerous patents relating to this oxidation process have been published, particularly between 1950 and 1970. These patents reveal the need to recycle a boron compound which is as pure as possible. Thus, as is in particular mentioned in French patents FR-B-1497519 and 1498351 in the name of the present Applicant, it is desirable to avoid the recycling of various organic impurities with the boric acid, because these impurities inhibit the oxidation reaction and lead to reactor fouling.

The processes described in the above patents involve the use, for the recovery of the boric acid for its recycling, a crystallization stage of the boric acid by cooling the aqueous phase from the hydrolysis zone and a stage of washing the cyrstallized acid with a solvent, such as methanol or a methanol-water mixture, as well as optionally a drying or dehydration stage for the boric acid prior to its recycling in the hydrocarbon oxidation stage.

These processes suffer from many disadvantages, the most important of which are associated with the use of specific equipment used in the mineral industry, such as crystallizers, centrifuges and rotary kilns, whose use is difficult and whose costs are high. Moreover, the use of a washing solvent such as methanol leads to a significant boron compound loss, which is more or less soluble in said alcohol and which alsc reacts therewith to form methanol-soluble methyl borate. It is also necessary to mention that the boric compound crystals obtained during these processes are relatively large, which limits their reactivity with respect to the alcohol formed in the oxidation stage and consequently reduces the alcohol selectivity of the complete process.

The process described in French patent application FR-A-2363516, published in 1978, suffers from the same disadvantages as those referred to hereinbefore for the processes described by the Applicant and in particular those linked with the use of the specific equipment of the mineral industry.

It is known and described more particularly in FR-B-1513001, that the drying and dehydration treatment also serves to at least partly convert the orthoboric acid into an acid with a lower degree of hydration, particularly metaboric acid, which is recycled to the oxidation stage and makes it possible to obtain a better alcohol yield.

Thus, although it is possible to use in the oxidation process both orthoboric acid, metaboric acid, boric anhydride and mixtures of these boron compounds, as is in particular described in French patent application FR-A-2209737, p 1, lines 14 to 21, it is preferable according to the latter to at least partly convert the orthoboric acid into metaboric acid, which is returned to the oxidation zone (p 5, lines 14 to 17). It is stressed that the teaching of FR-B-1513001 and FR-A-2209737 does not make it possible to obviate the aforementioned disadvantages and in particular those linked with the use of a specific equipment of the mineral industry.

The present invention proposes a technical solution completely different from that which has been used for 25 years and which makes it possible to limit to the minimum the use of specific mineral industry equipment and, in its preferred form, does not involve any use of such equipment.

In its broadest form, namely the part relating to the recycling of the boron compound, the process according to the present invention only uses a single specific mineral industry equipment, which makes it possible to recover the boric acid from its mixture with a compound having a boiling point higher than that of methyl borate. Usually the boric oxide to be recovered is suspended in an organic solvent and use is then made of a simple centrifuge or a simple filtering apparatus.

In its preferred performance form, with respect to the part relating to the recycling of the boron compound, the process according to the invention only uses distillation operations, which are easy to perform and involve relatively low maintenance and manpower costs as compared with the specific mineral industry equipment. Thus, in this preferred form, the boron compound is obtained suspended in the hydrocarbon which is oxidized and it is then possible to recycle this suspension without having to separate the boron compound.

The process according to the invention makes it possible to recycle a boron compound containing less impurities and in particular organic impurities than the recycles compound according to the prior art, whilst at the same time having an extremely small boron loss. It is also easy to perform and makes it possible to obtain a boron compound in extremely divided form, usually at least partly in the form of a sol, which makes it possible to obtain a higher alcohol selectivity than that obtained according to the prior art and is relatively time-constant.

More specifically, the present invention relates to a process for the oxidation of at least one saturated hydrocarbon selected from the group consisting of cyclohexane and cyclic and acyclic saturated hydrocarbons having 7 to 20 carbon atoms in their molecule, into a product incorporating the corresponding alcohol, according to which:

a) said hydrocarbon is oxidized in the liquid phase with the aid of a gas containing molecular oxygen, in the presence of at least one boron compound, forming esters with the alcohol formed during the oxidation and selected from the group consisting of boric oxides, in anhydrous or hydrated form and of general formula (I) $B_2O_3$, $xH_2O$, in which x is a number between 0 and 3, b) the reaction mixture obtained in stage a) and which contains at least one ester of said boron compound is hydrolyzed into a product incorporating orthoboric acid and an alcohol corresponding to said hydrocarbon, c) the reaction mixture obtained in stage b) is separated into a aqueous phase containing orthoboric acid and an organic phase containing an alcohol corresponding to said hydrocarbon and from which said alcohol is recovered, said process being characterized in that it comprises the following stages:

d) under methyl borate formation conditions, the aqueous phase obtained in stage c) is treated by methanol in a molar quantity at least equal to the theoretical quantity necessary for the formation of the methyl borate-methanol azeotrope and, in a distillation column, separation takes place of the methyl borate in the form of its azeotrope with methanol, which is recovered at the top of the column, and a phase having a higher boiling point than that of the methanol-methyl borate azeotrope and containing water, which is recovered at the bottom of the column, e) into a hydrolysis zone are introduced the methanol-methyl borate azeotrope recovered in stage d) and water, in a water:methyl borate molar ratio of approximately 1.3:1 to approximately 2.9:1 and in said zone methyl borate hydrolysis at least partly takes place, f) into a distillation column are introduced the product from the hydrolysis zone of stage e), at least one compound forming heteroazeotrope with methanol, said heteroazeotrope having a boiling point below that of the methanol-methyl borate azeotrope and at least one compound having a boiling point higher than that of the methyl borate, said compound not forming an azeotrope with a boiling point below that of said heteroazeotrope, g) at the top of the column used in stage f), said heteroazeotrope is recovered and is fed into a decanter, where separation takes place of the methanol from the compound forming said heteroazeotrope and said compound is recycled into the distillation column as reflux and at least partly as a charge of said compound to said column, h) at the bottom of the column used in stage f), recovery takes place of a mixture incorporating at least one boric oxide, in anhydrous or hydrated form, and said compound with a boiling point higher than that of methyl borate and i) recycling takes place to stage a) of the mixture recovered in stage h) or the boric oxide obtained by separation from said mixture recovered in stage h).

Stages a) of oxidation, b) hydrolysis and c) separation of an organic phase and an aqueous phase are of a conventional nature and their general conditions are well known in the art. These conditions will not be described here. Numerous documents refer to these conditions, e.g. Ullmann's Encyclopedia of Industrial Chemistry, Fifth, completely Revised Edition, vol. A8, pages 220 and 221, Benzene and its derivatives, edited by E. G. HANCOCK, LONDON, 1975, pages 238 to 251, and patents FR-B-1442272, FR-B-1497522, FR-B-1536937, FR-B-1549178, FR-B-1556968, FR-B-1524498, FR-B-1556980, U.S. Pat. No. 3,895,067 and U.S. Pat. No. 3,932,513.

In oxidation stage a), it is conventional practice to use a gas containing 2 to 25% by volume oxygen, e.g. a mixture of nitrogen and oxygen, air, optionally diluted by an inert gas such as nitrogen, but it is also possible to use a gas which is richer in oxygen such as oxygen-enriched air. Oxidation takes place under temperature and pressure conditions such that it is performed in the liquid phase. The oxidation temperature is generally approximately 100° to 250° C. and usually approximately 130° to 200° C. and the pressure is normally approximately 0.5 to 4 Megapascals (MPa).

During the oxidation stage a), the boron compound used is preferably selected from the group consisting of boric anhydride of general formula (I), in which x is equal to zero, metaboric acid of general formula (I) in which x is equal to 1, the mixtures of these two compounds and mixtures of metaboric acid and orthoboric acid containing elss than 60% and preferably less than 30% by weight of orthoboric acid of general formula (I), in which x is equal to 3.

When the boron compound used in the oxidation stage is one of the preferred compounds referred to hereinbefore, for the satisfactory operation of the process it is then necessary to choose the methyl borate hydrolysis conditions in stage e) in such a way that the product obtained is the desire dproduct, i.e. one of the preferred compounds referred to hereinbefore.

In stage b) of hydrolyzing the reaction mixture from the oxidation stage a), it is usual to use a water quantity of approximately 0.01 to approximate 1 times by weight, the weight of said reaction effluent, the hydrolysis temperature normally being approximately 20 to approximately 170° C. and the pressure approximately 0.1 to approximately 4 MPa. This hydrolysis reaction is very fast and normally lasts approximately 5 minutes to approximately 4 hours.

In stage c), the separation between an organic phase and an aqueous phase takes place under conventional conditions, e.g. in a decanter. The organic phase containing the alcohol formed during oxidation is then fed into a section for treating and recovering said alcohol. This treatment preferably comprises a first water-washing stage, which is normally followed by a saponification stage and optionally a second water-washing stage, followed by the recovery of the alcohol, e.g. by distillation or extraction with the aid of a solvent. This organic phase treatment is of a conventional nature and is e.g. described in several of the aforementioned documents. The washing water used in the first washing stage is preferably at least partly subsequently used in the hydrolysis stage b) of the reaction mixture obtained in stage a). In a preferred form, said washing water can comprise at least part of the water separated at the bottom of the column in methyl borate formation stage d).

Stage d) involving the formation of methyl borate and the separation in a distillation column (incorporating in its lower part a stripping zone and in its upper part an enrichment zone) of the methyl borate-methanol azeotrope at the top of the column and at the bottom of the column a higher boiling point phase containing water, can be carried out in two separate zones (an esterification reactor and a distillation column), or in one and the same distillation-reaction zone, in which the methyl borate formation reaction takes place simultaneously with the separation of the azeotrope which is recovered at the head of said zone. Normally use is made of at least 4 moles of methanol per mole of orthoboric acid. The methanol:orthoboric acid molar ratio is e.g. 4:1 to 20:1 and preferably 5:1 to 10:1 and usually use is made of a methanol quantity such that the ratio is approximately 6:1. The use of a methanol quantity at least equal to the theoretical quantity necessary for the formation of the methyl borate-methanol azeotrope (i.e. 4 moles of methanol per mole of orthoboric acid), or a methanol excess as defined hereinbefore, makes it possible to obtain the methyl borate-methanol azeotrope, which is recovered at the top of the distillation column. This methyl borate-methanol azeotrope contains 76.5% by weight methyl borate (i.e. 1 mole of methyl borate per mole of methanol).

This distillation column can operate at a pressure below, equal to or higher than atmospheric pressure. Preferably said distillation is performed at atmospheric pressure with a temperature at the bottom of the column of approximately 70° C. to approximately 100° C. Under these conditions and when operating with a methanol excess, e.g. in a reactive adiabatic-type column, the orthoboric acid conversion exceeds 99% and usually exceeds 99.5%. Thus, the unconverted orthoboric acid quantity recovered at the bottom of the column is very small.

In an advantageous embodiment of the invention, the distillation conditions are chosen in such a way as to obtain at the column bottom a product having a boiling point higher than that of the methyl borate-methanol azeotrope, which contains water and a very small amount of methanol, preferably below 1% and usually below 0.2% by weight based on the weight of said product. This can be obtained by operating under a given pressure at a temperature at the bottom of the column exceeding the boiling point of methanol.

Under these conditions, the excess methanol is e.g. drawn off from the column in a median part of the enrichment zone and is then recycled either to the methyl borate formation reactor, or into the actual column, e.g. at the introduction point of the charge incorporating the orthoboric acid and the water from stage c) and methanol. It is also possible to draw off the excess methanol, in part or in totality, with the methyl borate-methanol azeotrope and to feed said mixture into the methyl borate hydrolysis stage e) and then the product resulting from this is supplied to the distillation column of stage f), in which the methanol is all separated at the top in the form of a heteroazeotrope. Usually, at least a major part of the excess methanol is drawn off in the median area of the column enrichment zone. This distillation column used in stage d) is a conventional column normally having approximately 20 to 100 and usually approximately 30 to 80 theoretical plates. The stripping zone of this column normally has 1 to 20 and usually 2 to 10 theoretical plates. Above said stripping zone, the enrichment zone normally has 20 to 80 and most frequently 30 to 70 theoretical plates.

In a preferred embodiment of the invention, the methanol separated in the decanter during stage g), is recycled to the methyl borate formation stage d). In an advantageous embodiment of the invention, the compound having a higher boiling point than that of the methyl borate used is the hydrocarbon which undergoes oxidation in stage a).

The boric oxide or oxides in anhydrous or hydrated form of general formula (I), which form during the hydrolysis in stage e), are products obtained in stage h), at the bottom of the column used in stage f), mixed with the compound having a boiling point higher than that of methyl borate and usually in the form of a suspension in said compound, which are obtained from the methyl borate with a very good conversion level usually exceeding 95 molar % and most frequently approximately 100%, in the form of an extremely divided and relatively pure product. The mixture obtained in stage h) can be fed into a separation zone where the solid boric oxide or oxides are recovered and recycled to stage a). In a preferred embodiment of the invention, the solid boric oxide or oxides are obtained in the form of an extremely divided solid suspension, which is normally at least partly in sol form, in the hydrocarbon which has undergone oxidation, and in this case there is no separation of said boric oxide or oxides and said suspension is recycled to stage a).

The invention is particularly suitable for the oxidation of cyclohexane into an oxidation product containing cyclohexanol, which is normally present in majority form compared with the other oxidation products.

The following example illustrates the second object of the invention.

EXAMPLE 2

In a continuously operating unit, oxidation takes place of liquid cyclohexane by means of a gaseous mixture of oxygen and nitrogen containing 4% by volume oxygen. This gaseous mixture is introduced by the line (40) into the liquid cyclohexane, raised to a temperature of 165° C., contained in the reactor (A) and containing in suspended form essentially pure metaboric acid particles continuously introduced into the oxidation reactor. The operating pressure is 1 MPa. The flow rates of the cyclohexane and the essentially pure metaboric acid introduced into the reactor (A) are respectively 83 tonnes per hour (t/h) and 3.7 t/h. The cyclohexane is introduced by the line (150) at a rate of 62 t/h and by the line (19) at a rate of 21 t/h. The residence time in the oxidation reactor is 2 hours and the cyclohexane conversion level is 12%. The oxidation effluent is contacted with the water necessary for hydrolysis in the line (1) and the total mixture is introduced into the hydrolysis reactor (B). The water necessary for carrying out the hydrolysis comes by line (2) from the organic phase washing column (C1). The water quantity introduced by the line (2) is 7.4 t/h, i.e. a weight representing 0.089 times the weight of the oxidation effluent. The residence time in the hydrolysis reactor is 10 minutes, the temperature 145° C. and the pressure 1 MPa. The molar cyclohexanol selectivity is 83%.

The effluent of the hydrolysis reactor (B) is supplied by the line (3) into the decanter (B1), in which separation takes place of a light organic phase containing a small amount of orthoboric acid, from a heavy aqueous phase containing in solution most of the orthoboric acid present in the effluent of the reactor (B). The light organic phase is fed by the line (4) into the water washing column (C1), in which the washing water containing traces of the orthoboric acid from the methyl borate distillation column (C2) is introduced by the line (8). During this washing, the orthoboric acid present in the organic phase is extracted by the washing water and the heavy aqueous phase recovered at the bottom of the washing column (C1) is fed into the hydrolysis stage by the line (2). The light organic phase recovered at the head of the washing column (C1) is fed to the cyclohexanol purification and recovery section by the line (6).

The heavy aqueous phase containing in solution most of the orthoboric acid present in the effluent of the reactor (B) is recovered at the bottom of the decanter (B1) by the line (5). This aqueous phase which contains, besides the orthoboric acid to be recycled, soluble products and in particular cyclohexanol, cyclohexanone, acids and other organic byproducts formed during oxidation, is contacted in the line (9) with the methanol necessary for the formation of the methyl borate. The methanol quantity introduced into the line (9) by the line (17) is 11 t/h. This methanol comes from the decanter (D) of the distillation column (C3) for the heteroazeotropic mixture of 2,3-dimethyl butane and methanol. The product contained in the line (9) is mixed with the methanol drawn off from the column (C2) by the line (10) and the mixture, forming the charge for methyl borate preparation is introduced into the reactive distillation column (C2) by the line (11). This reactive distillation column has 65 theoretical plates. The charge is introduced into the column (C2) at the 25th plate from the bottom and the lateral methanol stream is drawn off at the 55th plate. The reflux level of the column (C2) is fixed at 1.2 and distillation takes place at the head of the column and at 54.6° C., 11.47 t/h of the methyl borate-methanol azeotrope, which is fed by the line (12) into the hydrolysis reactor (R1). At the bottom of the column are drawn off 10.34 t/h of an essentially aqueous product containing all the water-soluble organic products, traces of methanol and 0.21% by weight of non-esterified orthoboric acid. Most of this aqueous phase drawn off from the bottom of the column (C2) is fed by the line (8) to the washing column (C1), the remainder being discharged by the line (20). The product quantity rejected by the line (20) is 3.3 t/h.

Into the perfectly stirred hydrolysis reactor (R1) are introduced by the line (12) the methyl borate-methanol azeotrope and the stoichiometric water quantity necessary for the formation of metaboric acid using the line (14), i.e. 3.04 t/h. Hydrolysis of the methyl borate takes place at a temperature of 125° C. under an absolute pressure of 2 MPa in the perfectly stirred reactor (R1). The residence time of the methyl borate-methanol-water mixture in the reactor (R1) is fixed at 10 minutes.

The effluent of the reactor (R1) is continuously introduced by the line (60) into the distillation column (C3) operating under atmospheric pressure. This column has 43 theoretical plates and the effluent is introduced at ⅓ of the total column height starting from the bottom. Into the said column (C3) are also introduced by the line (15) and at the same level as the effluent from the reactor (R1) and in continuous manner, 21 t/h of cyclohexane. On starting up operations, into the column (C3) are introduced 10 tonnes of 2,3-dimethyl butane as compound forming with the methanol the heteroazeotrope having a boiling point below that of the methyl borate-methanol azeotrope. This compound forms with the methanol a heteroazeotrope incorporating 20% by weight methanol and whose boiling point is 45° C. Into the decanter of the product recovered at the head of the column are introduced continuously by the line (50) 0.32 t/h of water (i.e. 3% by weight based on the methanol weight). The product recovered at the head of the column by the line (16) is condensed and is then fed into the decanter (D), where recovery takes place of a heavy phase containing the water introduced by the line (50) and virtually all the methanol formed by the hydrolysis of the methyl borate. The heavy phase quantity recovered in the decanter by the line (17) is 11 t/h. The light phase is 2,3-dimethyl butane containing traces of methanol and is supplied by the line (18) to the head of the column (C3) in the form of reflux and at a rate of 43.2 t/h. The reflux level is maintained constant throughout the operation and is equal to 1. At the bottom of the column (C3) and at a temperature of 81° C. are drawn off 24.77 t/h of a suspension in cyclohexane of 15% by weight of a very finely divided solid, which is essentially pure metaboric acid. This suspension is recycled by the line (19) to the oxidation reactor (A).

After operating for 5,000 hours, the unit is stopped and the equipment inspected. There is no accumulation of deposits which may cast doubts on their operation. During the test, the cyclohexanol selectivity remained substantially constant and the hourly boric compound loss is below 5 kg.

We claim:

1. A process for the preparation of at least one boric oxide, in anhydrous or hydrated form and of general formula $B_2O_3$, $xH_2O$, in which x is a number from 0 to 3, by hydrolysis of methyl borate, said process comprising passing:
   (a) a hydrolyzate product comprising boric acid and methanol into a distillation column, said hydrolyzate having been produced in a hydrolysis zone from methyl borate and water in a molar ratio of water per mole of methyl borate of about 1.5:1 to about 2.5:1, and
   (b) at least one compound forming a heteroazeotrope with methanol, said heteroazeotrope having a boiling point below that of the methyl borate-methanol azeotrope, wherein:
   into said column is also introduced (c) at least one compound having a boiling point above that of methyl borate, said compound not forming an azeotrope with a boiling point below that of said heteroazeotrope;
   at the top of the column, said heteroazeotrope is recovered and fed into a decanter, in which the methanol is separated from the compound forming said heteroazeotrope, and said compound is recycled into the distillation column as reflux and as a charge for said column; and
   at the bottom of the column, a mixture is recovered having at least one boric oxide, in anhydrous or hydrated form, and the compound having a boiling point higher than that of methyl borate.

2. A process according to claim 1, wherein the compound forming a heteroazeotrope with methanol is selected from the group consisting of compounds forming a heteroazeotrope containing at least 10% by weight methanol in the heteroazeotrope.

3. A process according to claim 1, wherein the compound forming a heteroazeotrope with methanol is selected from among the group consisting of those whose heteroazeotrope has a boiling point lower by at least 2° C. than the boiling point of the methanol-methyl borate azeotrope.

4. A process according to claim 1, wherein the compound forming a heteroazeotrope with methanol is a hydrocarbon.

5. A process according to claim 4, wherein the compound forming a heteroazeotrope with methanol is selected from the group consisting of hydrocarbons having 4 to 6 carbon atoms in their molecule and no 6-membered ring.

6. A process according to claim 5, wherein the compound forming a heteroazeotrope with methanol is selected from the group consisting of 2-methanol pentane and 2,3-dimethyl butane.

7. A process according to claim 1, wherein the compound having a boiling point higher than that of methyl borate is a compound having a boiling point at least 2° C. higher than that of methyl borate.

8. A process according to claim 1, wherein the compound having a boiling point higher than that of methyl borate is a hydrocarbon.

9. A process according to claim 8, wherein the compound having a boiling point higher than that of methyl borate is selected from the group consisting of cyclohexane and saturated hydrocarbons having 7 to 20 carbon atoms in their molecule.

10. A process according to claim 1, wherein water in a quantity of at least 0.5% by weight, based on the weight of the methanol present, is introduced into the decanter.

11. A process according to claim 1, wherein the starting product for the preparation of at least one boric oxide, in anhydrous or hydrated form, is methyl borate, the methanol-methyl borate azeotrope or a methanol-methyl borate mixture containing more than 1 mole of methanol per mole of methyl borate.

12. A process according to claim 11, wherein the methyl borate used as the starting product for the preparation of at least one boric oxide, in anhydrous or hydrated form, is the product resulting from the reaction of orthoboric acid of formula $H_3BO_3$ on a methanol excess, based on the theoretical quantity necessary for the formation of methyl borate and optionally in the p presence of water.

13. A process according to claim 1, wherein the molar ratio in step (a) is about 1.8:1 to about 2.2:1.

14. A process according to claim 1, wherein the hydrolysis temperature is about 100°-180° C.

15. A process according to claim 1, wherein said distillation column has a reboiler, a bottom zone, an intermediate zone, and a top zone and wherein the hydrolyzate is introduced into the distillation column above the first theoretical plate and below the top zone, the compound having a boiling point higher than that of methyl borate is introduced into the distillation column at the bottom zone and below the point of introduction of the hydrolyzate, and the compound forming the heteroazeotrope with the methanol is introduced into the top zone or into said decanter.

16. A process for the oxidation of at least one saturated hydrocarbon selected from the group consisting of cyclohexane and cyclic and acyclic saturated hydrocarbons having 7 to 20 carbon atoms in their molecule, into a product incorporating the corresponding alcohol, according to which:
   (a) said hydrocarbon is oxidized in the liquid phase with the aid of a gas containing molecular oxygen, in the presence of at least one boron compound, forming esters with the alcohol formed during the oxidation and selected from the group consisting of b boric oxide, of the formula (I) $B_2O_3 \cdot xH_2O$, in which x is 0 or 1, mixtures thereof, and mixtures of betaboric acid and orthoboric acid, said mixture containing less than 60% by weight of orthoboric acid, (b) the reaction mixture obtained in stage (a) and which contains at least one ester of said boron compound is hydrolyzed into a product incorporating orthoboric acid and an alcohol corresponding to said hydrocarbon, (c) the reaction mixture obtained in stage (b) is separated into an aqueous phase containing orthoboric acid and an organic phase containing an alcohol corresponding to said hydrocarbon and from which said alcohol is recovered, said process including the regeneration of boric oxide by a process comprising the following stages:

(d) under methyl borate formation conditions, the aqueous phase obtained in stage (c) is treated by methanol in a molar quantity at least equal to the theoretical quantity necessary for the formation of the methyl borate-methanol azeotrope and, in a distillation column, separation takes place of the methyl borate in the form of its azeotrope with methanol and which is recovered at the top of the column, and a phase having a higher boiling point than that of the methanol-methyl borate azeotrope and containing water, which is recovered at the bottom of the column, (e) into a hydrolysis zone are introduced the methanol-methyl borate azeotrope recovered in stage (d) and water, in a water:methyl borate molar ratio of approximately 1.5:1 to approximately 2.6:1 and in which the hydrolysis conditions are such that formation takes place of either boric anhydride, or metaboric acid, or a mixture of these two compounds, or a mixture incorporating metaboric acid and orthoboric acid, said mixture containing less than 60% by weight orthoboric acid, (f) into a distillation column are introduced the product from the hydrolysis zone of stage (e), at least one compound forming a heteroazeotrope with methanol, said heteroazeotrope having a boiling point below that of the methanol-methyl borate azeotrope and at least one compound having a boiling point higher than that of the methyl borate, said compound not forming an azeotrope with a boiling point below that of said heteroazeotrope, (g) at the top of the column used in stage (f), said heteroazeotrope is recovered and is fed into a decanter, where separation takes place of the methanol from the compound forming said heteroazeotrope and said compound is recycled into the distillation column as reflux and at least partly as a charge of said compound to said column, (h) at the bottom of the column used in stage (f), recovery takes place of a mixture incorporating at least one boric oxide, in anhydrous or hydrated form, and said compound with a boiling point higher than that of methyl borate, and (i) recycling takes place to stage (a) of the mixture recovered in stage (h) or the boric oxide obtained by separation from said mixture recovered in stage (h).

17. A process according to claim 16, wherein stage d) is performed in a reaction-distillation zone.

18. A process according to claim 16, wherein the methanol separated in stage g) is recycled to the methyl borate formation stage d).

19. A process according to claim 16, wherein the organic phase separated in stage c) undergoes a water-washing prior to the recovery of the alcohol and the washing water is at least partly used in the hydrolysis stage b) of the reaction mixture obtained in stage a).

20. A process according to claim 19, wherein the water used for washing the organic phase separated in stage c) at least partly comes from the methyl borate formation stage d).

21. A process according to claim 16, wherein the saturated hydrocarbon is cyclohexane.

22. A process according to claim 16, wherein the compound having a higher boiling point than that of the methyl borate used in stage f) is the hydrocarbon subjected to oxidation in stage a).

23. A process according to claim 16, wherein said distillation column has a reboiler, a bottom zone, an intermediate zone, and a top zone and wherein the hydrolyzate is introduced into the distillation column above the first theoretical plate and below the top zone, the compound having a boiling point higher than that of methyl borate is introduced into the distillation column at the bottom zone and below the point of introduction of the hydrolyzate, and the compound forming the heteroazeotrope with the methanol is introduced into the top zone or into said decanter.

* * * * *